United States Patent
Hatch et al.

(10) Patent No.: US 12,084,594 B2
(45) Date of Patent: Sep. 10, 2024

(54) GALVANIZED METAL CORROSION INHIBITOR COMPOSITIONS AND METHODS OF USE

(71) Applicant: ECOLAB USA INC., St. Paul, MN (US)

(72) Inventors: Steven R. Hatch, Prior Lake, MN (US); Jothibasu Seetharaman, Pune (IN); Ashish Dhawan, Aurora, IL (US); Carter M. Silvernail, Burnsville, MN (US); Santanu Banerjee, Pune (IN); Pradeep Cheruku, Bolingbrook, IL (US)

(73) Assignee: ECOLAB USA Inc., St. Paul, MN (US)

( * ) Notice: Subject to any disclaimer, the term of this patent is extended or adjusted under 35 U.S.C. 154(b) by 175 days.

(21) Appl. No.: 17/186,631

(22) Filed: Feb. 26, 2021

(65) Prior Publication Data

US 2021/0301151 A1  Sep. 30, 2021

Related U.S. Application Data

(60) Provisional application No. 63/000,659, filed on Mar. 27, 2020.

(51) Int. Cl.
  *C08K 5/3447* (2006.01)
  *C09D 5/08* (2006.01)
  *C09D 179/02* (2006.01)

(52) U.S. Cl.
  CPC ........... *C09D 5/086* (2013.01); *C09D 179/02* (2013.01); *C08K 5/3447* (2013.01)

(58) Field of Classification Search
  None
  See application file for complete search history.

(56) References Cited

U.S. PATENT DOCUMENTS 4,235,838 A  11/1980  Redmore et al.
4,395,294 A   7/1983  Hobbins et al.
(Continued)

FOREIGN PATENT DOCUMENTS

EP  3345977 B1  10/2020
JP  S5773185 U   5/1982
(Continued)

OTHER PUBLICATIONS

PCT International Search Report and Written Opinion for PCT/US2021/019870, mailed May 31, 2021, 14 pages.

*Primary Examiner* — Shamim Ahmed
*Assistant Examiner* — Bradford M Gates
(74) *Attorney, Agent, or Firm* — Eric D. Babych; Barnes & Thornburg LLP

(57) ABSTRACT

A method of preventing formation of rust on a metal surface is provided. The method may include applying a polyamine onto the metal surface and applying a compound of formula (I) or salt thereof onto the metal surface. The compositions and methods disclosed herein may be used to inhibit corrosion of a metal surface in contact with an aqueous system.

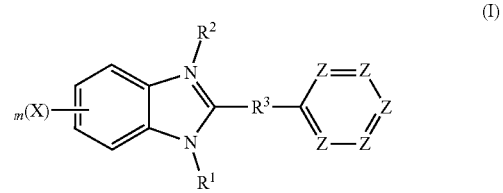

10 Claims, 2 Drawing Sheets

(56) References Cited

U.S. PATENT DOCUMENTS

| | | | |
|---|---|---|---|
| 5,435,860 | A | 7/1995 | Maki et al. |
| 6,479,103 | B1 | 11/2002 | Wichelhaus et al. |
| 7,291,402 | B2 | 11/2007 | Kazuhisa et al. |
| 8,585,964 | B2 | 11/2013 | Sotoudeh et al. |
| 9,051,654 | B2 | 6/2015 | Matsuda et al. |
| 9,757,811 | B2 | 9/2017 | Matsui et al. |
| 10,174,206 | B2 | 1/2019 | Matzdorf et al. |
| 10,202,694 | B2 | 2/2019 | Rane et al. |
| 2002/0197468 | A1 | 12/2002 | Sinko |
| 2005/0137298 | A1 | 6/2005 | Schneider |
| 2010/0178197 | A1* | 7/2010 | Sotoudeh ................ C23F 14/02 422/15 |
| 2012/0018053 | A1 | 1/2012 | Nagaya et al. |
| 2016/0348252 | A1* | 12/2016 | Rane ..................... C23F 11/184 |
| 2017/0181292 | A1* | 6/2017 | Tang .................. C23C 18/1834 |
| 2019/0144395 | A1 | 5/2019 | Cheruku et al. |
| 2019/0203362 | A1 | 7/2019 | Xie et al. |

FOREIGN PATENT DOCUMENTS

| | | |
|---|---|---|
| WO | 2010083112 A1 | 7/2010 |
| WO | 2016191672 A1 | 12/2016 |

\* cited by examiner

GALVANIZED METAL CORROSION INHIBITOR COMPOSITIONS AND METHODS OF USE

BACKGROUND

1. Field of the Invention

The present disclosure generally relates to compositions and methods for inhibiting white rust on galvanized metal surfaces in industrial water systems. More particularly, the disclosure pertains to a composition comprising a 2-substituted benzimidazole alone or in combination with a polyamine-based component where the composition can be introduced onto a galvanized metal surface.

2. Description of the Related Art

Galvanization is a protective zinc coating that is chemically bonded to a metal surface. The zinc coating protects the underlying metal from corrosion by providing a mechanical barrier to the environment as well as electrochemical resistance. Several galvanizing methods exist, such as electroplating, continuous galvanization, and hot-dip galvanization. Many industrial water systems, such as cooling water circulation systems, have such galvanized surfaces.

A common problem with galvanized coatings is white rust, which manifests itself as a white, waxy, fluffy, or powdery non-protective and porous deposit that rapidly forms on galvanized surfaces when the surface is exposed to humid and/or wet conditions. White rust can cause considerable damage to the zinc coating and is also detrimental to the coating's appearance. If untreated, white rust will continually corrode affected galvanized surfaces and eventually lead to early failure of the coating. With such a non-protective, porous deposit on the galvanized surface, the surface may form more white rust and rapidly corrode.

Current white rust corrosion prevention programs include a combination of pre-passivating the cooling tower combined with ongoing water chemistry management to support the viability of the passivation layer. In addition to the basic zinc carbonate protective layers, white rust preventatives include pretreatment with inorganic phosphate and chromate passivation. Such inorganic solutions have limited effectiveness and are steadfastly becoming the object of federal and local regulations due to environmental concerns.

BRIEF SUMMARY

A composition is disclosed that includes a polyamine and a compound of formula (I) or salt thereof,

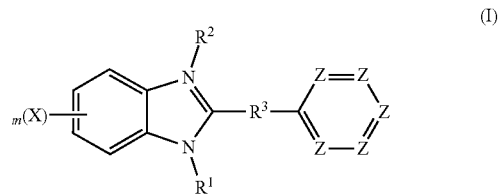

(I)

wherein X is independently hydrogen, halogen, or a substituted or unsubstituted $C_{1-5}$ alkyl group; m is 1, 2, 3, or 4; $R^1$ is hydrogen, a substituted or unsubstituted $C_1$-$C_{12}$ alkyl group, or a substituted or unsubstituted $C_4$-$C_6$ aryl group; $R^2$ is absent, hydrogen, a substituted or unsubstituted $C_1$-$C_{12}$ alkyl group, or a substituted or unsubstituted $C_4$-$C_6$ aryl group; $R^3$ is a bond or $CHR^4$; $R^4$ is hydrogen, halogen, $NR^5R^6$, or $OR^5$; wherein $R^5$ and $R^6$ are each independently hydrogen, a substituted or unsubstituted $C_1$-$C_{12}$ alkyl group, or a substituted or unsubstituted $C_4$-$C_6$ aryl group; and Z is independently nitrogen, CX, or $N^+R^5$.

In some aspects, X is independently hydrogen or halogen, $R^1$ is hydrogen, $R^2$ is absent, and $R^3$ is $CHR^4$.

In some aspects, the compound of formula (I) is

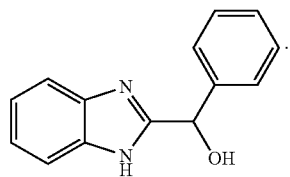 [SMILES: OC(c1ccccc1)c1nc2ccccc2[nH]1]

In some aspects, the polyamine is poly[oxy(methyl)-1,2-ethandiyl], alpha-(2-aminomethylethyl)-omega-(2-aminomethyl-ethoxy)-) functionalized with 1,2-propanediol, 3-chloro.

In other aspects, a method of preventing formation of rust on a metal surface is provided. The method may include applying a polyamine onto the metal surface and applying a compound of formula (I) or salt thereof onto the metal surface,

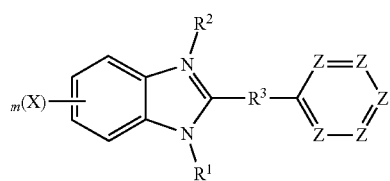

(I)

wherein X is independently hydrogen, halogen, or a substituted or unsubstituted $C_{1-5}$ alkyl group; m is 1, 2, 3, or 4; $R^1$ is hydrogen, a substituted or unsubstituted $C_1$-$C_{12}$ alkyl group, or a substituted or unsubstituted $C_4$-$C_6$ aryl group; $R^2$ is absent, hydrogen, a substituted or unsubstituted $C_1$-$C_{12}$ alkyl group, or a substituted or unsubstituted $C_4$-$C_6$ aryl group; $R^3$ is a bond or $CHR^4$; $R^4$ is hydrogen, halogen, $NR^5R^6$, or $OR^5$; wherein $R^5$ and $R^6$ are each independently hydrogen, a substituted or unsubstituted $C_1$-$C_{12}$ alkyl group, or a substituted or unsubstituted $C_4$-$C_6$ aryl group; and Z is independently nitrogen, CX, or $N^+R^5$.

In some aspects, the metal surface is a galvanized metal surface that is part of an industrial water system.

In some aspects, the compound of formula (I) and the polyamine are applied onto the metal surface by spraying an effective amount directly onto the metal surface.

In some aspects, the compound of formula (I) and the polyamine are applied onto the metal surface by dipping the metal surface into a solution containing the compound of formula (I) and the polyamine.

In some aspects, the method may further include applying one or more compounds selected from the group consisting of: other corrosion inhibitors, scale inhibitors, fluorescent tracers, water treatment polymers, and combinations thereof.

In some aspects, the method may further include applying one or more other corrosion inhibitors selected from the group consisting of: phosphates; phosphonates; phosphinates; silicates; molybdate; tungstate; borate; zinc and its salts; vanadate; chromate; polycarboxylates; and combinations thereof.

In some aspects, the method may further include mixing the compound of formula (I) and the polyamine before applying to the metal surface.

In some aspects, the rust is white rust.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific aspects disclosed may be readily utilized as a basis for modifying or designing other aspects for carrying out the same purposes of the present disclosure. It should also be realized by those skilled in the art that such equivalent aspects do not depart from the spirit and scope of the disclosure as set forth in the appended claims.

DETAILED DESCRIPTION

Figure 1:
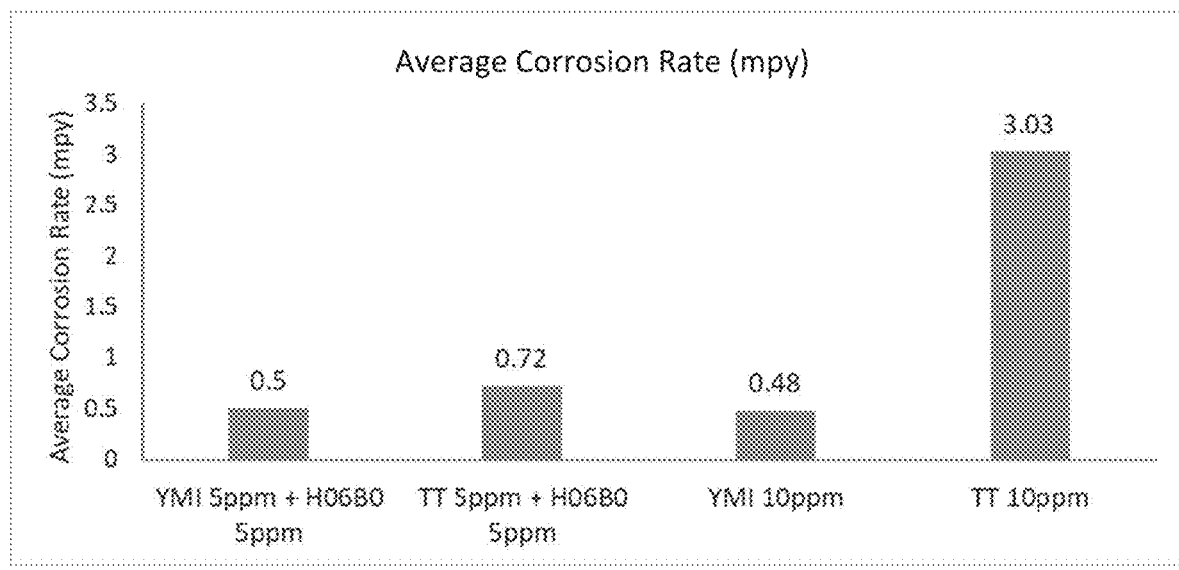
FIG. 1 shows the average corrosion rate of a galvanized disk exposed to various chemical treatments.

Various aspects are described below. The relationship and functioning of the various elements of the aspects may better be understood by reference to the following detailed description. However, aspects are not limited to those illustrated below. In certain instances, details may have been omitted that are not necessary for an understanding of aspects disclosed herein.

"Alkyl" refers to a straight-chain or branched alkyl substituent. Examples of such substituents include methyl, ethyl, propyl, isopropyl, n-butyl, sec-butyl, isobutyl, tert-butyl, pentyl, isoamyl, hexyl, and the like.

"Aryl" refers to an unsubstituted or substituted aromatic carbocyclic substituent, as commonly understood in the art, and the term "$C_6$-$C_{10}$ aryl" includes phenyl and naphthyl. It is understood that the term aryl applies to cyclic substituents that are planar and comprise 4n+2n electrons, according to Huckel's Rule.

"Cycloalkyl" refers to a cyclic alkyl substituent containing from, for example, about 3 to about 8 carbon atoms, preferably from about 4 to about 7 carbon atoms, and more preferably from about 4 to about 6 carbon atoms. Examples of such substituents include cyclopropyl, cyclobutyl, cyclopentyl, cyclohexyl, cycloheptyl, cyclooctyl, and the like. The cyclic alkyl groups may be unsubstituted or further substituted with alkyl groups, such as methyl groups, ethyl groups, and the like.

"Halogen" or "halo" refers to F, Cl, Br, and I.

"Heteroaryl" refers to a monocyclic or bicyclic 5- or 6-membered ring system, wherein the heteroaryl group is unsaturated and satisfies Huckel's rule. Non-limiting examples of heteroaryl groups include furanyl, thiophenyl, pyrrolyl, pyrazolyl, imidazolyl, 1,2,3-triazolyl, 1,2,4-triazolyl, isoxazolyl, oxazolyl, isothiazolyl, thiazolyl, 1,3,4-oxadiazol-2-yl, 1,2,4-oxadiazol-2-yl, 5-methyl-1,3,4-oxadiazole, 3-methyl-1,2,4-oxadiazole, pyridinyl, pyrimidinyl, pyrazinyl, triazinyl, benzofuranyl, benzothiophenyl, indolyl, quinolinyl, isoquinolinyl, benzimidazolyl, benzoxazolinyl, benzothiazolinyl, quinazolinyl, and the like.

"Oxo" refers to an oxygen atom double-bonded to a carbon atom.

Compounds of the present disclosure may be substituted with suitable substituents. The term "suitable substituent," as used herein, is intended to mean a chemically acceptable functional group, preferably a moiety that does not negate the activity of the compounds. Such suitable substituents include, but are not limited to, halo groups, perfluoroalkyl groups, perfluoro-alkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C═O)— groups, heterocylic groups, cycloalkyl groups, amino groups, alkyl- and dialkylamino groups, carbamoyl groups, alkylcarbonyl groups, alkoxycarbonyl groups, alkylaminocarbonyl groups, dialkylamino carbonyl groups, arylcarbonyl groups, aryloxy-carbonyl groups, alkylsulfonyl groups, and arylsulfonyl groups. In some aspects, suitable substituents may include halogen, an unsubstituted $C_1$-$C_{12}$ alkyl group, an unsubstituted $C_4$-$C_6$ aryl group, or an unsubstituted $C_1$-$C_{10}$ alkoxy group. Those skilled in the art will appreciate that many substituents can be substituted by additional substituents.

In some aspects, a composition is disclosed that may include a polyamine and a compound or salt thereof of formula (I). The compound of formula (I) has the formula shown below

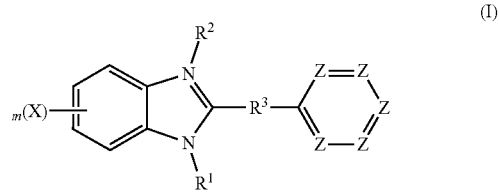

In some aspects, X is independently hydrogen, halogen, or a substituted or unsubstituted $C_{1-5}$ alkyl group, and m may be 1, 2, 3, or 4. In some aspects, $R^1$ may be hydrogen, a substituted or unsubstituted $C_1$-$C_{12}$ alkyl group, or a substituted or unsubstituted $C_4$-$C_6$ aryl group. In some aspects, $R^2$ may be absent, hydrogen, a substituted or unsubstituted $C_1$-$C_{12}$ alkyl group, or a substituted or unsubstituted $C_4$-$C_6$ aryl group. In some aspects, $R^3$ may be a bond or $CHR^4$. In some aspects, $R^4$ may be hydrogen, halogen, $NR^5R^6$, or $OR^5$. In some aspects, $R^5$ and $R^6$ are each independently hydrogen, a substituted or unsubstituted $C_1$-$C_{12}$ alkyl group, or a substituted or unsubstituted $C_4$-$C_6$ aryl group.

The X substituent or substituents can occupy any available position on the benzimidazole ring. Thus, in certain aspects, the X substituent or substituents can be located at the 4-position, 5-position, 6-position, and/or 7-position of the benzimidazole. In certain aspects, the X substituent is at the 5-position.

The number of X substituents, m, can be 1, 2, 3, or 4. If m is 2, 3, or 4, the X substituents can occupy any open position and can be positioned ortho-, meta-, or para- to each other.

In certain aspects, the salt of the compound of formula (I) may be any salt, such as a chloride salt, bromide salt, iodide salt, sulfate salt, fluoride salt, perchlorate salt, acetate salt, trifluoroacetate salt, phosphate salt, nitrate salt, carbonate salt, bicarbonate salt, formate salt, chlorate salt, bromated salt, chlorite salt, thiosulfate salt, oxalate salt, cyanide salt, cyanate salt, tetrafluoroborate salt, and the like. In some aspects, salt of the compound of formula (I) may be a hydrochloride or sulfate salt.

In some aspects, Z is independently nitrogen, CX, or $N^+R^5$.

In some aspects, Z is CX.

In some aspects, X is hydrogen and m is 4. In some aspects, X is absent.

In some aspects, $R^1$ is hydrogen.

In some aspects, $R^2$ is absent.

In some aspects, $R^3$ is a bond. In some aspects, $R^3$ is $CHR^4$.

In some aspects, $R^4$ is hydrogen. In some aspects, $R^4$ is halogen.

In some aspects, $R^4$ is $NR^5R^6$. In some aspects, $R^4$ is $OR^5$.

In some aspects, $R^5$ is a substituted or unsubstituted $C_1$-$C_{12}$ alkyl group. In some aspects, $R^5$ is hydrogen. In some aspects, $R^5$ is a substituted or unsubstituted $C_4$-$C_6$ aryl group.

In some aspects, one Z is nitrogen and the rest are CX.

In some aspects, at least two Zs are nitrogen and the rest are CX.

In some aspects, $R^3$ is a bond and at least one Z is nitrogen.

In some aspects, X is independently hydrogen or halogen, $R^1$ is hydrogen, $R^2$ is absent, and $R^3$ is $CHR^4$.

In some aspects, the compound or salt thereof of formula (I) is

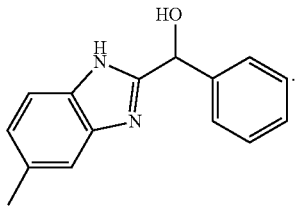 [SMILES: Cc1ccc2[nH]c(C(O)c3ccccc3)nc2c1]

In some aspects, the compound or salt thereof of formula (I) is

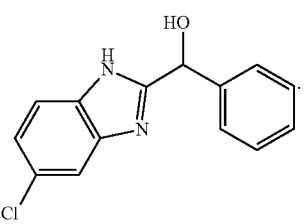 [SMILES: OC(c1ccccc1)c1nc2cc(Cl)ccc2[nH]1]

In some aspects, the compound or salt thereof of formula (I) is

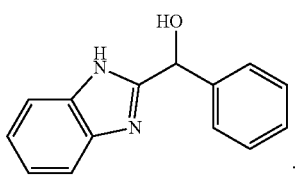 [SMILES: OC(c1ccccc1)c1nc2ccccc2[nH]1]

In some aspects, the compound or salt thereof of formula (I) is

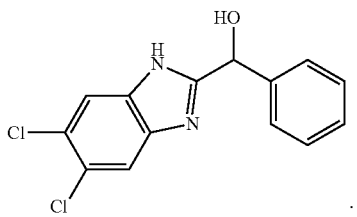 [SMILES: OC(c1ccccc1)c1nc2cc(Cl)c(Cl)cc2[nH]1]

In some aspects, the compound or salt thereof of formula (I) is

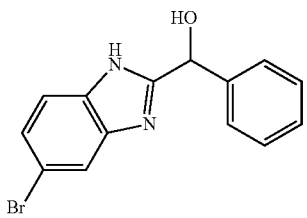

In some aspects, the compound or salt thereof of formula (I) is

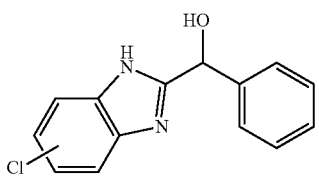

In some aspects, the compound or salt thereof of formula (I) is

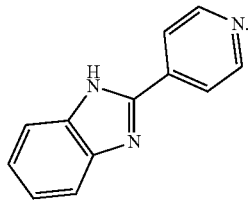 [SMILES: c1ccc2[nH]c(-c3ccncc3)nc2c1]

In some aspects, the compound or salt thereof of formula (I) is

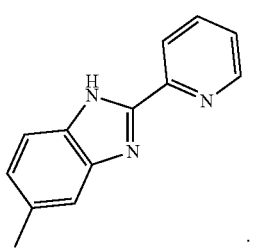 [SMILES: Cc1ccc2[nH]c(-c3ccccn3)nc2c1]

In some aspects, the compound or salt thereof of formula (I) is

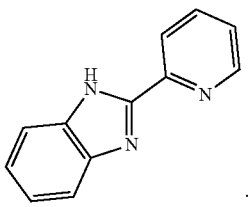 [SMILES: c1ccc(-c2nc3ccccc3[nH]2)nc1]

In some aspects, the compound or salt thereof of formula (I) is

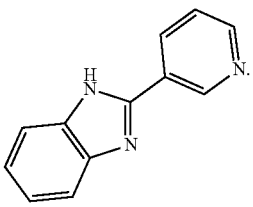 [SMILES: c1cncc(-c2nc3ccccc3[nH]2)c1]

In some aspects, the compound or salt thereof of formula (I) is

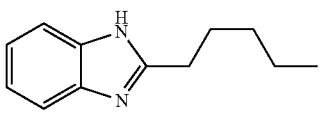

In some aspects, the compound or salt thereof of formula (I) is

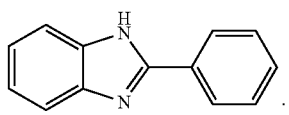 [SMILES: c1ccc(-c2nc3ccccc3[nH]2)cc1]

In some aspects, the composition may include a compound or salt thereof of formula (Ia),

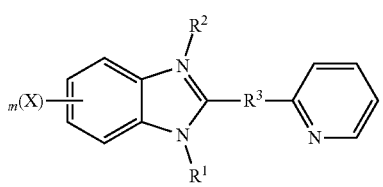

where X is independently hydrogen, halogen, or a substituted or unsubstituted $C_{1-5}$ alkyl group, and m is 1, 2, 3, or 4; $R^1$ is hydrogen, a substituted or unsubstituted $C_1$-$C_{12}$ alkyl group, or a substituted or unsubstituted $C_4$-$C_6$ aryl group; $R^2$ is absent, hydrogen, a substituted or unsubstituted $C_1$-$C_{12}$ alkyl group, or a substituted or unsubstituted $C_4$-$C_6$ aryl group; and $R^3$ is a bond or $CHR^4$. In some aspects, $R^4$ may be hydrogen, halogen, $NR^5R^6$, or $OR^5$. In some aspects, $R^5$ and $R^6$ are each independently hydrogen, a substituted or unsubstituted $C_1$-$C_{12}$ alkyl group, or a substituted or unsubstituted $C_4$-$C_6$ aryl group.

In some aspects, the compound or salt thereof is of formula (II),

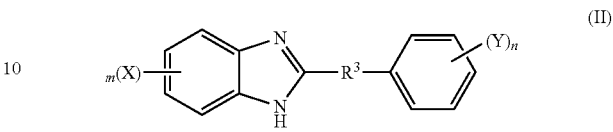

where X is independently hydrogen, halogen, or a substituted or unsubstituted $C_{1-5}$ alkyl group; m is 1, 2, 3, or 4; $R^3$ is a bond or $CHR^4$; Y is independently hydrogen, halogen, or a $C_{1-5}$ alkyl group; and n is 1, 2, 3, 4, or 5. In some aspects, $R^4$ may be hydrogen, halogen, $NR^5R^6$, or $OR^5$. In some aspects, $R^5$ and $R^6$ are each independently hydrogen, a substituted or unsubstituted $C_1$-$C_{12}$ alkyl group, or a substituted or unsubstituted $C_4$-$C_6$ aryl group.

In some aspects, Y is hydrogen.

In some aspects, Y is independently hydrogen and halogen.

As described herein, m can be 1, 2, 3, or 4. If m is 2, 3, or 4, the X substituents can occupy any open position and can be positioned ortho-, meta-, or para- to each other. The number of Y substituents, n, can be 1, 2, 3, or 4. If n is 2, 3, or 4, the Y substituents can occupy any open position and can be positioned ortho-, meta-, or para- to each other.

In some aspects, the concentration of the compound or salt thereof of formula (I), formula (Ia), or formula (II) in the composition may range from about 1 wt % to about 50 wt %, about 5 wt % to about 50 wt %, about 10 wt % to about 50 wt %, about 15 wt % to about 50 wt %, about 20 wt % to about 50 wt %, about 20 wt % to about 45 wt %, about 25 wt % to about 45 wt %, or about 25 wt % to about 40 wt %.

In some aspects, the composition may include water.

In some aspects, the composition may be a homogenous mixture. In some aspects, the composition may be a solution.

In some aspects, the polyamine is poly[oxy(methyl)-1,2-ethandilyl], alpha-(2-aminomethylethyl)-omega-(2-aminomethyl-ethoxy)-) functionalized with 1,2-propanediol, 3-chloro.

In some aspects, the polyamine is formed from a polyoxypropylene diamine. In some aspects, the polyamine is of the formula $[CH(OH)CH(OH)CH_2]_2N—[CH(CH_3)CH_2O]_X—N[CH_2CH(OH)CH(OH)]_2$. X is from 1 to about 20. In this aspect, the amine groups of the compound are hydroxyl-functionalized.

In some aspects, the polyamine is made by reacting a compound characterized by repeating oxypropylene units in the backbone and has the chemical formula $H_2N—(CH(CH_3)CH_2O)_Z—CH_2CH(CH_3)NH_2$, with glycidol (2,3-epoxy-1-propanol), where Z is 1 to 3.

In some aspects, the composition may have a weight ratio of the compound of formula (I) to the polyamine of about 4:1. In some aspects, the weight ratio ranges from about 2:1 to about 6:1.

In other aspects, a method of preventing formation of rust on a metal surface is provided. The method may include applying a polyamine onto the metal surface and applying a compound of formula (I) or salt thereof onto the metal surface.

The disclosure provides methods of using heterocyclic compounds and formulations comprising heterocyclic compounds that are particularly useful for inhibiting corrosion of metallic components in industrial water systems. Adding to an aqueous system a benzimidazole capable of undergoing chelation with a metal provides excellent metal corrosion resistance. In particular, adding benzimidazoles substituted with a 2-pyridyl or a benzyl alcohol to an aqueous system in contact with a metal surface leads to excellent corrosion inhibition for metals, such as copper. Moreover, while benzotriazoles and benzimidazoles are generally unstable in the presence of oxidizing halogen compounds, the compounds of the present disclosure are capable of undergoing 1,2-chelation with a metal to impart exemplary protection of the metal in the presence of oxidizing halogen compounds. In particular, 2-(2-pyridyl)benzimidazoles provide greater protection against corrosion than benzimidazole, 2-phenylbenzimidazole, and tolyltriazole in the presence of oxidizing halogen compounds. While not wishing to be bound by any particular theory, it is believed that the compounds of the present disclosure form a protective film that is essentially impenetrable by common oxidizing halogen compounds due to bidentate chelation of the corrosion inhibitor with the metal surface. Thus, in certain aspects, the methods of the present disclosure provide protection against metal corrosion in aqueous systems which employ oxidizing halogen compounds as biocides.

In some aspects, the disclosure provides a method for inhibiting or preventing corrosion of a metal surface in contact with an aqueous system. The method may include adding to the aqueous system any composition described in the present disclosure. For example, the composition may include a compound of formula (I) and a polyamine.

"Industrial water system" means any system that circulates water. Non-limiting examples of "industrial water systems" include cooling systems, boiler systems, heating systems, membrane systems, papermaking systems, or any other systems that circulate water.

The compositions comprising the polyamine and the compounds of formulae (I), (Ia), and/or (II) may provide corrosion protection for galvanized metals. The compositions may prevent rust formation. In some aspects, the rust is white rust.

The term "white rust" refers to a type of corrosion product affecting galvanized surfaces characterized as an accumulation of white, fluffy, or waxy non-protective zinc corrosion product that adheres to the zinc surface of galvanized steel.

One way to passivate the surfaces is to allow the zinc coating to develop a natural nonporous surface of basic zinc carbonate during initial start-up of the cooling tower. This natural chemical barrier helps prevent or slow further rapid corrosion of the zinc coating from the environment as well as from normal cooling tower operation. White rust is also a form of zinc carbonate that has a different porous structure, rate of formation, and density than the protective zinc carbonate barrier described above.

While the compounds of formulae (I), (Ia), and (II) can be added to an aqueous system at any dosage rate, the compounds of formulae (I), (Ia), and (II) are generally added to an aqueous system at a dosage rate of from about 0.01 ppm to about 500 ppm. In certain aspects, a compound of formula (I), (Ia), or (II) is added to an aqueous system at a dosage rate of from about 0.01 ppm to about 100 ppm. In certain aspects, a compound of formula (I), (Ia), or (II) is added to an aqueous system at a dosage rate of from about 0.01 ppm to about 100 ppm, from about 0.01 ppm to about 75 ppm, from about 0.01 ppm to about 50 ppm, from about 0.01 ppm to about 25 ppm, from about 0.01 ppm to about 10 ppm, from about 0.01 ppm to about 5 ppm, from about 0.1 ppm to about 100 ppm, from about 0.1 ppm to about 75 ppm, from about 0.1 ppm to about 50 ppm, from about 0.1 ppm to about 25 ppm, from about 0.1 ppm to about 10 ppm, from about 0.1 ppm to about 5 ppm, from about 1 ppm to about 100 ppm, from about 1 ppm to about 75 ppm, from about 1 ppm to about 50 ppm, from about 1 ppm to about 25 ppm, from about 1 ppm to about 10 ppm, from about 5 ppm to about 100 ppm, from about 10 ppm to about 100 ppm, from about 25 ppm to about 100 ppm, from about 50 ppm to about 100 ppm, or from about 80 ppm to about 100 ppm.

In certain aspects, the aqueous system is a cooling water system. The cooling water system can be a closed loop cooling water system or an open loop cooling water system. In certain aspects, a compound of formula (I), (Ia), or (II) is added to a closed loop cooling water system at a dosage rate of from about 0.01 ppm to about 200 ppm. In certain aspects, a compound of formula (I), (Ia), or (II) is added to an open loop cooling water system at a dosage rate of from about 0.01 ppm to about 20 ppm.

The compounds of formulae (I), (Ia), and (II) are contacted with a metal surface by any suitable method. In certain aspects, a solution of a compound of formula (I), (Ia), or (II) is contacted with a metal surface by immersion, spraying, or other coating techniques. In certain aspects, a solution of a compound of formula (I), (Ia), or (II) is introduced into the water of the aqueous system by any conventional method and is fed into the aqueous system on either a periodic or continuous basis.

In one aspect, introducing the composition onto the galvanized surface includes incorporating the method into a hot dip manufacturing process. For example, the metal would first be dipped in melted zinc at 450° C. (temperature at which iron/steel and zinc share great affinity) where the metal would be protected with a zinc coating. The next step in the manufacturing process would be to dip the zinc-coated metal into the composition comprising the compound of formula (I), (Ia), or (II) and a polyamine.

In another aspect, such introduction onto the metal surface includes spraying a solution of the composition directly onto the surface, including surfaces in industrial water systems. In one aspect, the composition is mixed with a foaming agent to form a mixture and the mixture is subsequently sprayed onto the galvanized metal surface using any suitable spraying device. Foaming agents may include surfactants, such as alkoxylated alcohols, polyethylene glycol, or any other suitable surfactant. In alternative embodiments, the composition may be physically applied onto the surface by rolling using a paint roller or the like, brushing using a paintbrush or the like, swabbing using a mop or the like, or by using any other suitable method or technique.

In some aspects, the compound of formula (I), (Ia), or (II) and the polyamine may be applied onto the metal surface independently and in any order.

In another aspect, the composition is reintroduced onto the surface one or more times after one or more time intervals to "overlay" the barrier or "re-passivate" the surface. Ongoing overlaying steps to renew the corrosion-inhibitory barrier and/or to re-passivate the galvanized surfaces are also contemplated. As determined on a case-by-case basis, the method may include a plurality of different compositions and overlaying the barrier may include introducing a different one or more of the corrosion-reducing compositions onto the galvanized metal surface(s).

In some aspects, the compositions disclosed herein may include a fluorescent organic compound. In certain aspects, the fluorescent organic compound may be selected from rhodamine or derivatives thereof, an acridine dye, fluorescein or derivatives thereof, and combinations thereof. In certain aspects, the compositions disclosed herein may include a fluorescent tagged polymer.

Those skilled in the art will appreciate that the polyamine and the compound of formula (I), (Ia), or (II) can be added to an aqueous system or applied onto the surface of a metal alone or in combination with other corrosion inhibitors or treatment chemicals. Multiple corrosion inhibitors can be dosed as a combined corrosion inhibitor formulation or each corrosion inhibitor can be added separately, including two or more compounds of formula (I), (Ia), and/or formula (II). Moreover, a compound of formula (I), (Ia), or (II) can be added to an aqueous system in combination with a variety of additional corrosion inhibitors including, but not limited to, triazoles, benzotriazoles (e.g., benzotriazole or tolyltriazole), benzimidazoles, orthophosphate, polyphosphates, phosphonates, molybdates, silicates, oximes, and nitrites. The compounds of formulae (I), (Ia), and (II) also can be added to an aqueous system in combination with a variety of additional additives, such as treatment polymers, anti-microbial agents, anti-scaling agents, colorants, fillers, buffers, surfactants, viscosity modifiers, chelating agents, dispersants, deodorants, masking agents, oxygen scavengers, and indicator dyes.

The compositions of the present disclosure may include from about 0 to 10 weight percent of the polyamine and from about 10 to about 100 weight percent of the compound of formula (I), with the balance being adjunct components and water. More preferably, the polyamine is present from about 2 to 10 weight percent and the compound of formula (I) is present from about 20 to about 100 weight percent, with the balance being adjunct components and water. Preferred blends include about 10 weight percent of the polyamine and about 90 weight percent of the compound of formula (I). More preferably, the blend includes about 40 weight percent of the polyamine and about 60 weight percent compound of formula (I). Most preferably, the blend is comprised of about 60 weight percent of the polyamine and about 40 weight percent compound of formula (I).

The dosage range for adding or applying the polyamine may range from 0.01 ppm to about 200 ppm. In some aspects, the polyamine dosage may range from about 0.01 ppm to about 50 ppm, from about 0.01 ppm to about 10 ppm, or from about 0.01 ppm to about 5 ppm. In some aspects, the polyamine dosage may be about 0.5 ppm.

The dosage range for adding or applying the compound of formula (I) may range from 0.01 ppm to about 200 ppm. In some aspects, the dosage may range from about 0.01 ppm to about 50 ppm, from about 0.01 ppm to about 10 ppm, or from about 0.01 ppm to about 5 ppm. In some aspects, the dosage may be about 2 ppm.

EXAMPLES

A three-electrode electrochemical cell was used where the working electrode was a galvanized disk. Two steel electrodes functioned as one reference and the other the counter electrode. The test solution was a mix of corrosive water and candidate inhibitor to be evaluated. Corrosive water generally included calcium 200 ppm (as $CaCO_3$); magnesium 200 ppm (as $CaCO_3$); chloride 500 ppm; and bicarbonate 150 ppm. 190 ml of test solution was used in each test and was continuously stirred using a magnetic stirrer while maintained at 80+/−2° F. Measurements were made in 5 hour intervals until high corrosion rate damaged working electrode galvanized surface.

Efficacy of the corrosion inhibitor compositions was determined by electrochemical corrosion rates by measuring polarization resistance. Cathodic and anodic slopes were determined by Tafel scan before the polarization run. The scans were run using a Gamry Potentiostat/Galvanostat set at 0.1 mV/sec.

Example 1

Total chemistry (corrosion inhibitor+polyamine) dosed in this experiment was about 10 ppm. The weight ratio of corrosion inhibitor to polyamine was about 1:1. FIG. 1 shows the average corrosion rate in mpy for various treatments. The compound YMI refers to compound 1 shown below. TT refers to tolytriazole and H0680 is a poly[oxy(methyl)-1,2-ethandilyl], alpha-(2-aminomethylethyl)-omega-(2-aminomethyl-ethoxy)-) functionalized with 1,2-propanediol, 3-chloro.

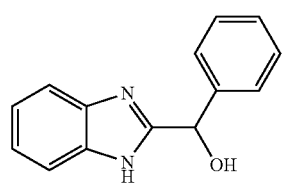

Compound 1

Example 2

Figure 2:
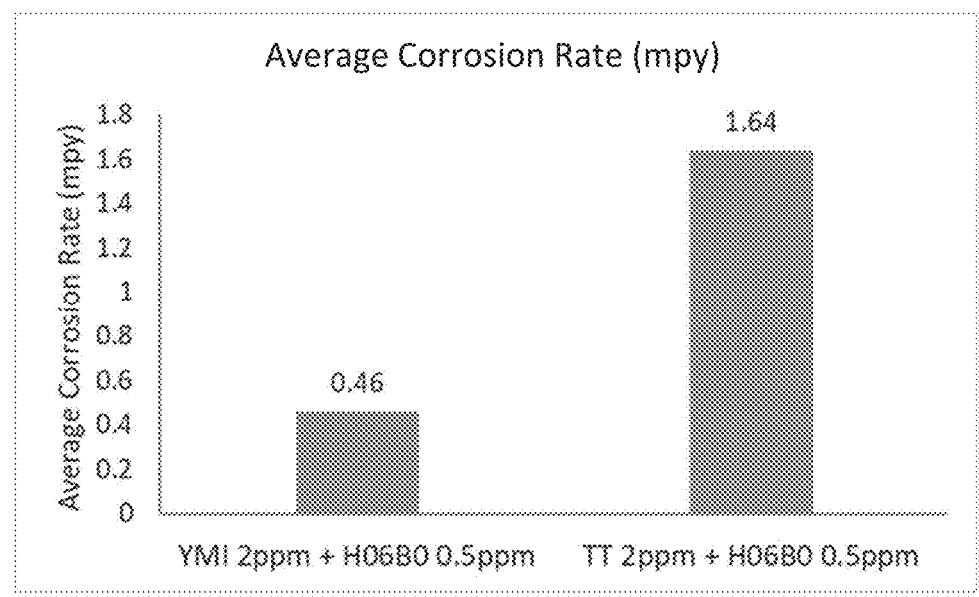
FIG. 2 shows the average corrosion rate of a galvanized disk exposed to a lower dosage chemical treatments.

Total chemistry (corrosion inhibitor+polyamine) dosed in this experiment was about 2.5 ppm. The weight ratio of corrosion inhibitor to polyamine was about 4:1. FIG. 2 shows the average corrosion rate in mpy for various treatments.

Any composition disclosed herein may comprise, consist of, or consist essentially of any of the compounds/components disclosed herein. In accordance with the present disclosure, the phrases "consist essentially of," "consists essentially of," "consisting essentially of," and the like limit the scope of a claim to the specified materials or steps and those materials or steps that do not materially affect the basic and novel characteristic(s) of the claimed invention.

As used herein, the term "about" refers to the cited value being within the errors arising from the standard deviation found in their respective testing measurements, and if those errors cannot be determined, then "about" refers to within 10% of the cited value.

All of the compositions and methods disclosed and claimed herein can be made and executed without undue experimentation in light of the present disclosure. While this invention may be embodied in many different forms, there are described in detail herein specific preferred aspects of the invention. The present disclosure is an exemplification of the principles of the invention and is not intended to limit the invention to the particular aspects illustrated. In addition, unless expressly stated to the contrary, use of the term "a" is intended to include "at least one" or "one or more." For example, "a compound" is intended to include "at least one compound" or "one or more compounds."

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various aspects described herein. It should also be understood that various changes and modifications to the presently preferred aspects described herein will be apparent to those skilled in the art. Such changes and modifications can be made without departing from the spirit and scope of the invention and without diminishing its intended advantages. It is therefore intended that such changes and modifications be covered by the appended claims.

What is claimed is:

1. A method of preventing formation of rust on a metal surface, comprising:
applying a compound of formula (I) onto the metal surface,

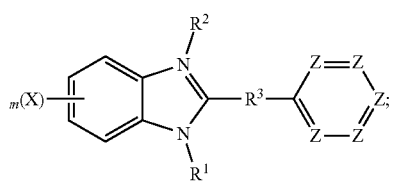
(I)

and
applying a polyamine onto the metal surface, wherein the polyamine comprises poly[oxy(methyl)-1,2-ethandiyl], alpha-(2-aminomethylethyl)-omega-(2-aminomethyl-ethoxy)-) functionalized with 1,2-propanediol, 3-chloro,
wherein X is independently hydrogen, halogen, or a substituted or unsubstituted $C_{1-5}$ alkyl group;
m is 1, 2, 3, or 4;
$R^1$ is hydrogen, a substituted or unsubstituted $C_1$-$C_{12}$ alkyl group, or a substituted or unsubstituted $C_4$-$C_6$ aryl group;
$R^2$ is absent, hydrogen, a substituted or unsubstituted $C_1$-$C_{12}$ alkyl group, or a substituted or unsubstituted $C_4$-$C_6$ aryl group;
$R^3$ is a bond or $CHR^4$;
$R^4$ is hydrogen, halogen, $NR^5R^6$, or $OR^5$; wherein $R^5$ and $R^6$ are each independently hydrogen, a substituted or unsubstituted $C_1$-$C_{12}$ alkyl group, or a substituted or unsubstituted $C_4$-$C_6$ aryl group; and
Z is independently nitrogen, CX, or $N^+R^5$.

2. The method of claim 1, wherein
X is independently hydrogen or halogen;
$R^1$ is hydrogen;
$R^2$ is absent; and
$R^3$ is $CHR^4$.

3. The method of claim 1, wherein the compound of formula (I) is

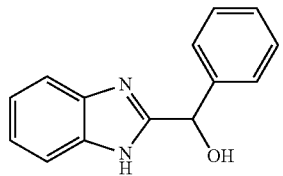

4. The method of claim 1, wherein the metal surface is a galvanized metal surface that is part of an industrial water system.

5. The method of claim 1, wherein the compound of formula (I) and the polyamine are applied onto the metal surface by spraying directly onto the metal surface.

6. The method of claim 1, wherein the compound of formula (I) and the polyamine are applied onto the metal surface by dipping the metal surface into a solution containing the compound of formula (I) and the polyamine.

7. The method of claim 1, further comprising applying one or more compounds selected from the group consisting of: other corrosion inhibitors, scale inhibitors, fluorescent tracers, water treatment polymers, and combinations thereof.

8. The method of claim 1, further comprising applying one or more other corrosion inhibitors selected from the group consisting of: phosphates; phosphonates; phosphinates; silicates; molybdate; tungstate; borate; zinc and its salts; vanadate; chromate; polycarboxylates; and combinations thereof.

9. The method of claim 1, wherein the rust is white rust.

10. The method of claim 1, further comprising mixing the compound of formula (I) and the polyamine before applying to the metal surface.

* * * * *

UNITED STATES PATENT AND TRADEMARK OFFICE
CERTIFICATE OF CORRECTION

PATENT NO. : 12,084,594 B2  
APPLICATION NO. : 17/186631  
DATED : September 10, 2024  
INVENTOR(S) : Steven R. Hatch et al.

Page 1 of 1

It is certified that error appears in the above-identified patent and that said Letters Patent is hereby corrected as shown below:

In the Specification

In Column 2, Lines 21-22, delete "poly[oxy(methyl)-1,2-ethandilyl]" and insert --poly[oxy(methyl)-1,2-ethanediyl]--.

In Column 8, Lines 44-45, delete "poly[oxy(methyl)-1,2-ethandilyl]" and insert --poly[oxy(methyl)-1,2-ethanediyl]--.

In Column 12, Lines 19-20, delete "poly[oxy(methyl)-1,2-ethandilyl]" and insert --poly[oxy(methyl)-1,2-ethanediyl]--.

In the Claims

In Column 13, Claim 1, Lines 41-42, delete "poly[oxy(methyl)-1,2-ethandilyl]" and insert --poly[oxy(methyl)-1,2-ethanediyl]--.

Signed and Sealed this  
Fifteenth Day of April, 2025

Coke Morgan Stewart  
*Acting Director of the United States Patent and Trademark Office*